US012310799B2

(12) United States Patent
Moore et al.

(10) Patent No.: US 12,310,799 B2
(45) Date of Patent: May 27, 2025

(54) MINIMALLY INVASIVE SURGERY LASER GUIDE

(71) Applicant: Wright Medical Technology, Inc., Memphis, TN (US)

(72) Inventors: Jesse G. Moore, Germantown, TN (US); John White, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 365 days.

(21) Appl. No.: 17/759,136

(22) PCT Filed: Apr. 9, 2021

(86) PCT No.: PCT/US2021/070364
§ 371 (c)(1),
(2) Date: Jul. 20, 2022

(87) PCT Pub. No.: WO2021/212131
PCT Pub. Date: Oct. 21, 2021

(65) Prior Publication Data
US 2023/0038459 A1    Feb. 9, 2023

Related U.S. Application Data

(60) Provisional application No. 63/011,405, filed on Apr. 17, 2020.

(51) Int. Cl.
*A61B 90/13*    (2016.01)
*A61B 17/17*    (2006.01)
(Continued)

(52) U.S. Cl.
CPC .............. *A61B 90/13* (2016.02); *A61B 17/17* (2013.01); *A61B 34/30* (2016.02); *A61B 2017/564* (2013.01); *A61B 2090/366* (2016.02)

(58) Field of Classification Search
CPC ...................................................... A61B 90/13
See application file for complete search history.

(56) References Cited

U.S. PATENT DOCUMENTS

| 5,375,495 A | 12/1994 | Bosten et al. |
| 6,578,459 B2 | 6/2003 | Waite |

(Continued)

FOREIGN PATENT DOCUMENTS

| WO | 2013152790 A1 | 10/2013 |
| WO | 2017070523 A1 | 4/2017 |

OTHER PUBLICATIONS

International Search Report and Written Opinion for PCT/US2021/070364 issued Jun. 30, 2021.

(Continued)

*Primary Examiner* — Olivia C Chang
(74) *Attorney, Agent, or Firm* — DUANE MORRIS LLP

(57) ABSTRACT

Various embodiments of a surgical instrument are disclosed. The surgical instrument includes a handle, a working element extending from the handle configured to be positioned internal of a target site while the handle is external to the target site, and a laser guide configured to generate at least one emitted marker. The emitted marker corresponds to movement of the working element internal of the target site. Various embodiments of methods using the surgical instrument are also disclosed.

15 Claims, 7 Drawing Sheets

(51) Int. Cl.
  *A61B 34/30*  (2016.01)
  *A61B 17/56*  (2006.01)
  *A61B 90/00*  (2016.01)

(56) References Cited

U.S. PATENT DOCUMENTS

| | | |
|---|---|---|
| 7,383,073 B1 | 6/2008 | Abovitz et al. |
| 7,398,719 B2 | 7/2008 | Peot et al. |
| 2004/0073225 A1 | 4/2004 | Subba Rao |
| 2007/0173946 A1* | 7/2007 | Bonutti .............. A61B 17/1717 623/20.14 |
| 2011/0106092 A1 | 5/2011 | Fisher et al. |
| 2012/0130378 A1 | 5/2012 | Marsh et al. |
| 2013/0204272 A1 | 8/2013 | Bonutti |
| 2014/0100620 A1 | 4/2014 | Mullaney |
| 2017/0000572 A1 | 1/2017 | Moctezuma de la Barrera et al. |
| 2017/0354425 A1 | 12/2017 | Zaima et al. |
| 2019/0231443 A1 | 8/2019 | McGinley et al. |
| 2019/0366080 A1 | 12/2019 | Siddiqui |

OTHER PUBLICATIONS

Extended European Search Report issued in connection with corresponding European Patent Application No. 21788950.1, Dec. 18, 2023, 7 pages.

* cited by examiner

MINIMALLY INVASIVE SURGERY LASER GUIDE

CROSS-REFERENCE TO RELATED APPLICATION

This application is a National Stage Application, filed under 35 U.S.C. 371, of International Patent Application No. PCT/US2021/070364, filed on Apr. 9, 2021, which claims priority to U.S. Provisional Application No. 63/011,405, filed on Apr. 17, 2020, the entireties of which are incorporated herein by reference.

TECHNICAL FIELD

This application relates generally to minimally invasive surgery (MIS) systems, and, more specifically, MIS surgical guides.

BACKGROUND

Various illumination and guide elements for minimally invasive surgery are known. For example, U.S. Pat. Appl. Pub. No. 2012/0004508 discloses a minimally invasive surgical system with an illuminator that includes a visible color component illumination source and a hardware non-visible fluorescence emission illumination source. The illuminator outputs target image illumination light in a first spectrum where the first spectrum includes at least a portion of the visible spectrum. The illuminator also outputs target image illumination light in a second spectrum, where the second spectrum includes non-visible light with a wavelength the same as a wavelength in an emission from a fluorophore.

Similarly, U.S. Pat. No. 9,232,951 discloses a method for aligning a bone cutting guide on a tibia may involve coupling a cutting guide alignment device and an attached cutting guide with a tibia, adjusting the alignment device in a varus/valgus orientation, adjusting the alignment device in an anterior/posterior orientation, attaching the cutting guide to the tibia, and removing the alignment device from the cutting guide, leaving the cutting guide attached to the tibia. The adjustments to the alignment device may be made according to vertically and horizontally oriented laser lights emitted from the alignment device. As the alignment device is adjusted, the bone cutting guide attached to the alignment device changes position relative to the tibia.

None of the prior art systems have been found to be completely adequate for minimally invasive surgical procedures.

SUMMARY

In various embodiments, a surgical instrument is disclosed. The surgical instrument includes a handle, a working element extending from the handle configured to be positioned internal of a target site while the handle is external to the target site, and a laser guide configured to generate at least one emitted marker. The emitted marker corresponds to movement of the working element internal of the target site In various embodiments, a system is disclosed. The system includes a surgical instrument and a first position sensor. The surgical instrument includes a handle, a working element extending from the handle configured to be positioned internal of a target site while the handle is external to the target site, and a laser guide configured to generate at least one emitted marker. The emitted marker corresponds to movement of the working element internal of the target site. The first position sensor is configured to be coupled to a target site and is configured to provide one or more signals indicative of movement of the target site in at least one axis of movement relative to the surgical instrument.

In various embodiments, a method of forming an osteotomy is disclosed. The method includes a step of positioning a surgical instrument at a first location relative to a target site. The surgical instrument includes a handle, a working element extending from the handle configured to be positioned internal of the target site while the handle is external to the target site, and a laser guide. At least one emitted marker is projected on a surface of the target site. The at least one emitted marker is configured to correspond to movement of the working element internal of the target site. At least one cut in a bone is formed by pivoting the surgical instrument on a travel path denoted by the at least one emitted marker.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
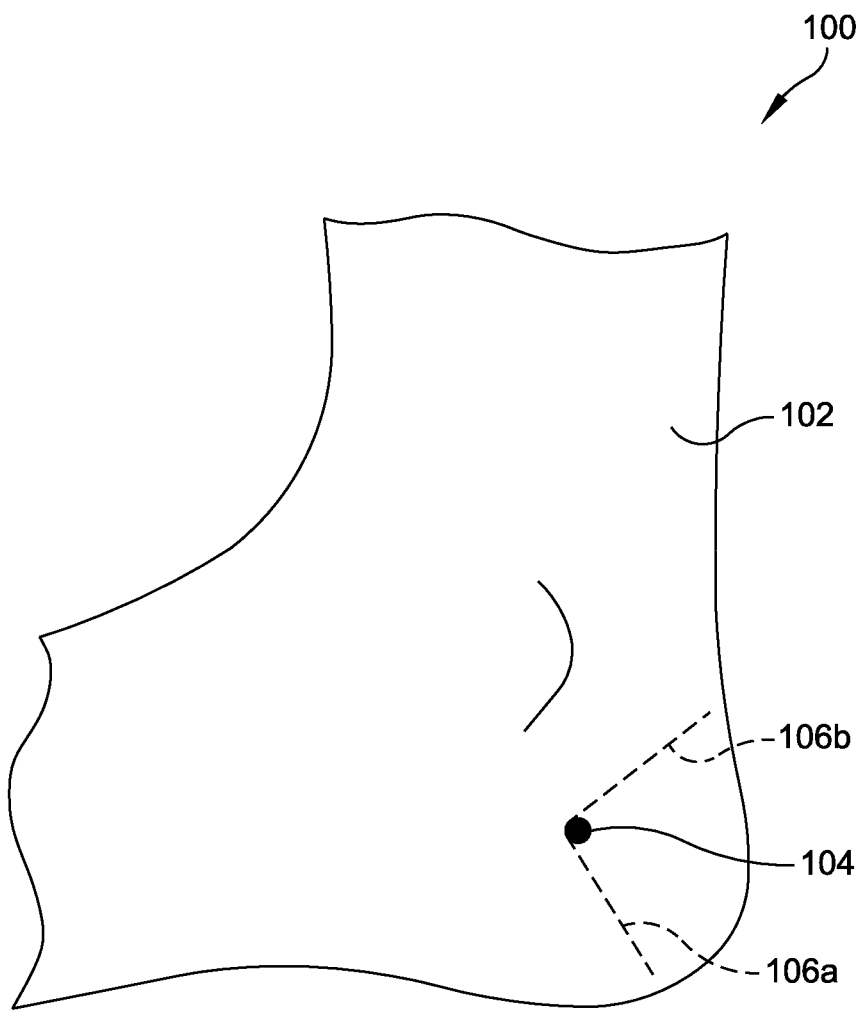
FIG. 1 illustrates a target site including one or more guide markings corresponding to one or more internal surgical operations, in accordance with some embodiments.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a system for providing guidance during a minimally invasive surgery (MIS) procedure is disclosed. The system includes a surgical instrument having at least one laser guide coupled thereto. The laser guide is configured to project one or more lines or areas onto a predetermined portion of a target site. The projected lines and/or areas correspond to one or more internal surgical operations to be performed using the surgical instrument, such as, for example, one or more internal cutting operations corresponding to an osteotomy. In some embodiments, the surgical system includes at least one position sensor configured to provide signals corresponding to movement of at least one of a surgical instrument or a target site.

Figure 2:
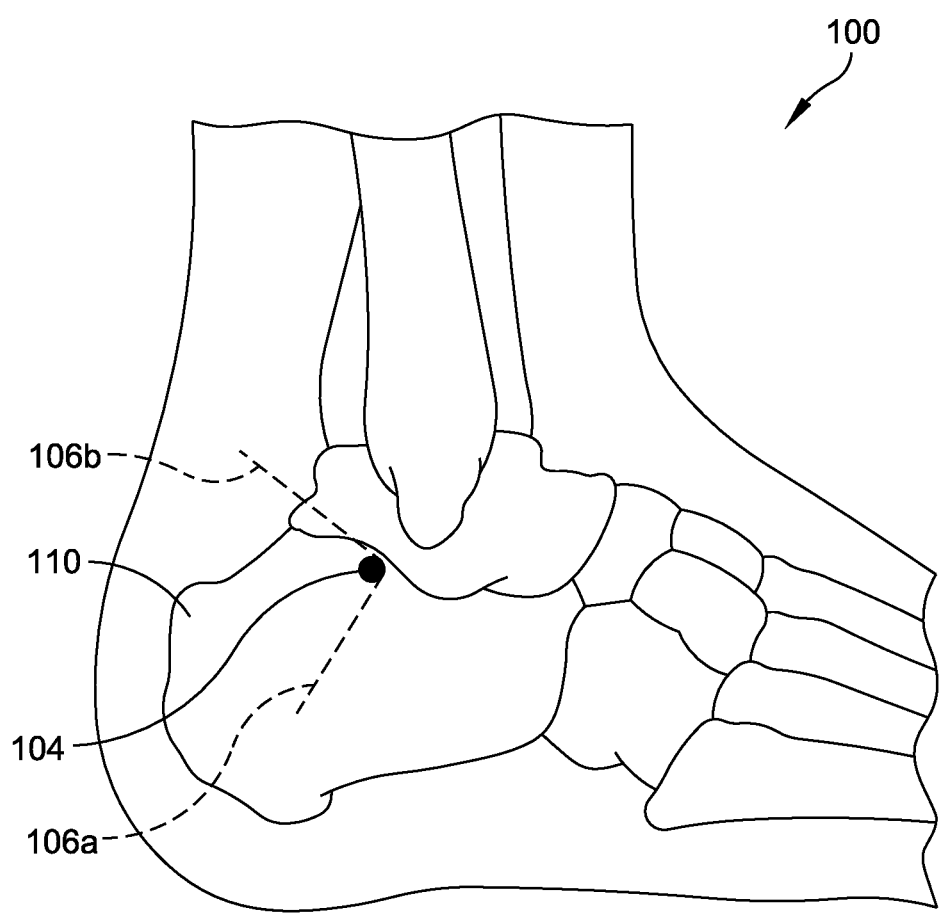
FIG. 2 illustrates an internal view of the target site of FIG. 1 including the one or more guide markings, in accordance with some embodiments.

FIG. 1 illustrates a target site 100 including one or more guide markings 106a, 106b corresponding to one or more internal surgical operations, in accordance with some embodiments. FIG. 2 illustrates an internal view of the target site 100 including the one or more guide markings 106a, 106b, in accordance with some embodiments. The target site 100 may include an anatomical structure 102 of a surgical patient, such as, for example a limb, foot, hand, and/or other extremity of a patient. In the illustrated embodiment, the target site 100 corresponds to a foot, and more specifically to a tarsal position including the calcaneus, although it will be appreciated that the disclosed systems and methods may be adapted for other target sites and/or surgical operations.

In some embodiments, the target site 100 includes one or more guide markings 106a, 106b formed a surface 112 of the target site 100. FIG. 1 illustrates the guide markings 106a, 106b formed on the surface 112 of the target site 100 and FIG. 2 illustrates an internal view of the target site 100 having the guide markings 106a, 106b projected onto internal structures, such as the calcaneus 110. In the illustrated embodiments, the surface 112 of the target site 100 includes the epidermis, although it will be appreciated that embodiments including open surgical procedures may have guide markings 106a, 106b formed on one or more other anatomical structures, such as, for example, directly on a bone.

The guide markings 106a, 106b are configured to correspond to a surgical procedure to be performed at the target site 100. For example, in the illustrated embodiment, the guide markings 106a, 106b correspond to a plurality of cuts to be formed in a calcaneus during an osteotomy procedure. The guide markings 106a, 106b may further correspond to individual cuts to be formed in a bone (or other anatomical structure) and/or may define an area to be removed from a bone (or other anatomical structure). For example, in the illustrated embodiment, the guide markings 106a, 106b correspond to two cuts to be formed in a calcaneus 110 to remove a portion of the calcaneus 110.

Figure 3:
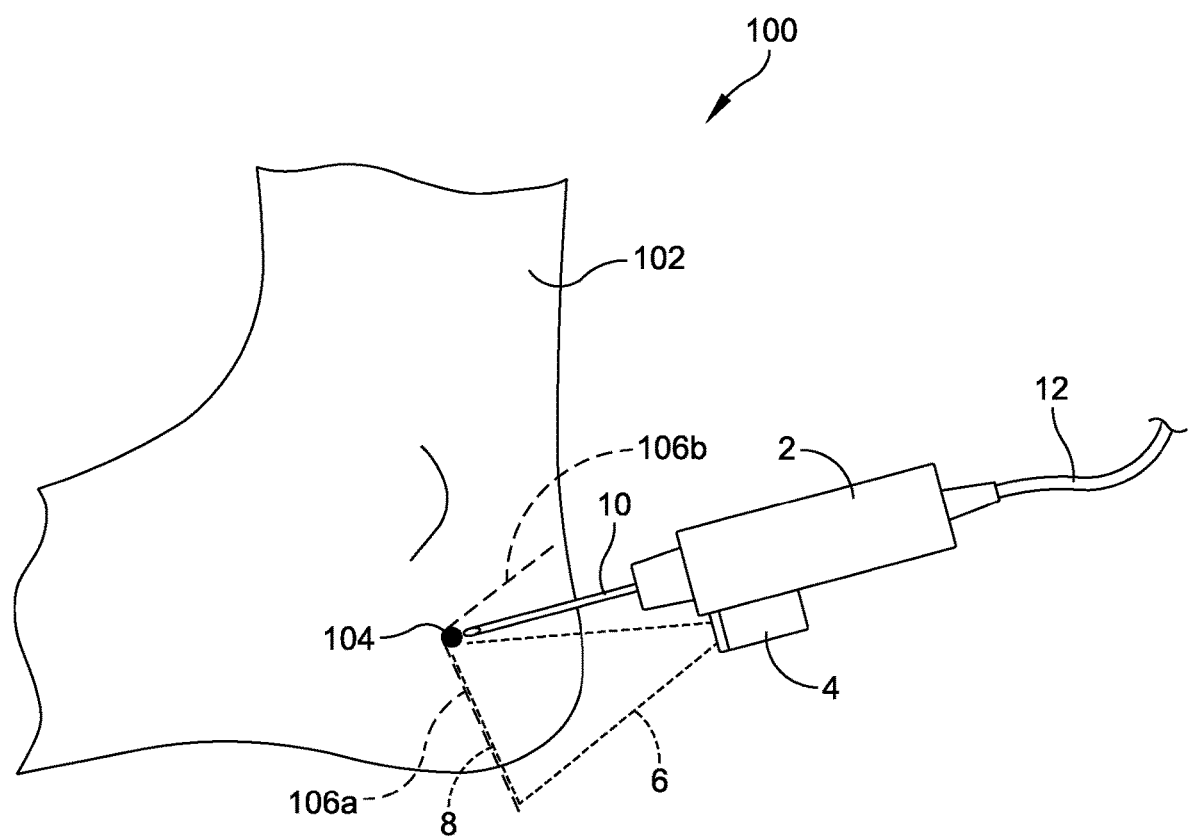
FIG. 3 illustrates a surgical instrument including a laser guide positioned at a first position with respect to the target site of FIG. 1, in accordance with some embodiments.

FIG. 3 illustrates a surgical instrument 2 including a laser guide 4, in accordance with some embodiments. The surgical instrument 2 may include any suitable working element 10 for performing one or more MIS procedures. For example, in the illustrated embodiment, the working element 10 includes a cutting element (e.g., blade, burr, etc.) configured to form cuts in a bone. Although embodiments are discussed herein including a cutting element, it will be appreciated that other MIS instruments, such as, for example, drills, saws, reamers, plates, positioning elements, etc.

The working element 10 of the surgical instrument 2, such as a cutting element, may be define a central axis that is aligned with and/or positioned with respect to a central axis defined by a handle 3 of the surgical instrument 2. The working element 10 (or other MIS element) is positioned internally through one or more openings 104 (e.g., keyhole surgery holes, arthroscopic portals, or ports) formed in the surface 112 of the target site 100. The illustrated surgical instrument 2 includes a handheld surgical instrument, although it will be appreciated that the disclosed systems and methods may be applied to other surgical instruments, such as, for example, robot-operated surgical instruments. Although embodiments are discussed herein including a laser guide 4 coupled to the surgical instrument 2, it will be appreciated that laser guides may be coupled to one or more additional surgical instruments, such as a guide, clamp, targeting system, etc. in addition to and/or in the alternative to the laser guide 4 coupled to the surgical instrument 2.

In some embodiments, the surgical instrument 2 is configured to be positioned at a target site 100 such that the surgical instrument 2 may be pivoted such that a portion of the surgical instrument 2 positioned interior to the target site 100 through the opening 104, such as a portion of the working element 10, moves in an opposite, pivoting direction from a portion of the surgical instrument 2 positioned exterior to the target site 100, such as the handle portion 3 of the surgical instrument 2. For example, in the illustrated embodiment, the surgical instrument 2 includes a working element 10 defining a central axis that is aligned with a central axis of a handle 3. The working element 10 can be partially and/or completely inserted through the opening 104 while maintaining the handle 3 external of the target site 100. The opening 104 in the target site 100 defines a pivot point between the portion of the surgical instrument 2 internal of the target site, e.g., the working element 10, and the portion external of the target site, e.g., handle 3.

The laser guide 4 is configured to generate one or more emissions 6 on one or more predetermined emission paths. The one or more emissions are configured to project at least one emitted marker 8 onto the surface 112 of the target site 100. The emitted marker 8 may include a dot, line, area, and/or any other predetermined pattern generated by the one or more emissions 6. In some embodiments, the emitted marker 8 has a predetermined shape corresponding to a shape of one or more of the guide markers 106a, 106b formed on the surface 112 of the target site 100. For example, in the illustrated embodiment, the laser guide 4 is configured to generate an emitted marker 8 having a linear (i.e., line) shape corresponding to a line defined by one of the guide markers 106a, 106b. In some embodiments, the emitted marker 8 may include a shape different from guide markers 106a, 106b. For example, in some embodiments, the guide markers 106a, 106b include linear marks and the at least one emitted marker 8 defines an area corresponding to an area delineated by the guide markers 106a, 106b.

In some embodiments, the emitted marker 8 may include one or more predetermined colors corresponding to different positions and/or orientations of the surgical instrument 2 with respect to the target site 100. For example, in some embodiments, the emitted marker 8 may include a first marker having a first color denoting one or more positions and a second marker having a second color denoting one or more boundary zones with respect to the target site. In some embodiments, the emitted marker 8 may transition from a first color (or set of colors) to a second color (or set of colors) to signal movement and/or position of a working element 10. For example, in some embodiments, the emitted marker 8 may have a first color when the working element 10 and/or other portion of the surgical instrument 2 is in a desired position and/or plane and may have a second color when the working element 10 out of a desired plane or position. It will be appreciated that the color of the emitted marker 8 may be changed to indicate the type of alignment issues, e.g., a first color for a first degree of freedom, a second color for a second degree of freedom, etc.

In some embodiments, the emitted marker 8 is configured to correspond to internal movement of a portion of the surgical instrument 2, such as, for example, internal movement of the cutting instrument 10. For example, the cutting instrument 10 may be configured to form one or more cuts in a bone, such as the calcaneus 110, when the surgical instrument 2 is pivoted, moved, or otherwise manipulated within the opening 104 formed in the surface 112 of the target site 100. The emitted marker 8 may be configured to illustrate internal movement of the cutting instrument 10, for example, by corresponding to an internal movement path of the cutting instrument 10, internal position of the cutting instrument 10, future position of the cutting instrument 10, and/or providing any other indication of internal movement of the cutting instrument 10.

In some embodiments, the laser guide 4 is configured to provide movement of the emitted marker 8 that is opposite of the movement of a handle 12 of a surgical instrument 2. For example, in embodiments including pivoting movement of the surgical instrument 2, a direction of internal movement of the cutting instrument 10 is opposite a direction of movement of the handle 12 external of the target site 100. The laser guide 4 may be configured to provide movement of the emitted marker 8 that mimics internal movement of the cutting instrument 10 in order to maintain a visual indication of the internal position of the cutting instrument 10. Such movement may be provided by any suitable mechanism, such as, for example, a motor, pivoting element, gyroscope, etc. The mechanism may be formed integrally with the laser guide 4 and/or external to the laser guide 4. For example, in some embodiments, a pivoting element may be configured to couple the laser guide 4 to the surgical instrument 2 to provide movement of the emission maker 8 that is opposite of the movement of a handle 12 of the surgical instrument 2.

In some embodiments, the laser guide 4 is configured to maintain a fixed position of the emitted marker independent of movement of the surgical instrument 2. For example, in some embodiments including pivoting movement of the surgical instrument 2, the laser guide 4 is configured to maintain a predetermined location for the emitted marker 8 on the surface 112 of the target site 100. The laser guide 4 may be configured to move the emitted marker 8 to compensate for movement of the surgical instrument 2 such that the emitted marker 8 maintains a fixed position on the surface 112 of the target site 100. Compensatory movement may be provided by any suitable mechanism, such as, for example, a motor, pivoting element, gyroscope, etc. The mechanism may be formed integrally with the laser guide 4 and/or external to the laser guide 4. For example, in some embodiments, a pivoting element may be configured to couple the laser guide 4 to the surgical instrument 2 and provide compensatory movement to the laser guide 4 to maintain the emitted marker 8 in a predetermined position. The predetermined position may be fixed and/or adjusted by a user.

In some embodiments, the laser guide 4 may be formed integrally with and/or be electrically connected to the surgical instrument 2. For example, in some embodiments, the laser guide 4 is formed integrally with and included in a housing of the surgical instrument 2. In other embodiments, one or more electrical connections may be formed between the laser guide 4 and the surgical instrument 2. For example, a power circuit of the laser guide 4 may be configured to connect to and/or be formed integrally with a power circuit of the surgical instrument 2. In some embodiments, the laser guide 4 is self-contained and includes circuits independent of the surgical instrument. For example, in some embodiments, the laser guide 4 includes an independent power connection and/or internal battery power configured to provide power to the laser guide independent of power provided to the surgical instrument 2.

FIG. 3 illustrates the surgical instrument 2 positioned at a first position with respect to the target site 100 such that the emitted marker 8 corresponds to a first guide marker 106a formed on the surface 112 of the target site 100. A first surgical operation, such as a first bone cut, is performed using the surgical instrument 2. Movement of the surgical instrument 2, such as internal movement of the cutting instrument 10, is guided by the position of the emitted marker 8 and the first guide marker 106a. For example, in some embodiments, a surgeon and/or robotic surgical system pivots (or otherwise moves) the surgical instrument 2 to cause internal movement of the cutting instrument 10. The movement of the cutting instrument 10 is illustrated by the emitted marker 8. The surgeon or robotic surgical system maintains alignment between the emitted marker 8 and the first guide marker 106a during movement of the cutting instrument 10 to form a first predetermined cut in a bone, such as the calcaneus 110.

Figure 4:
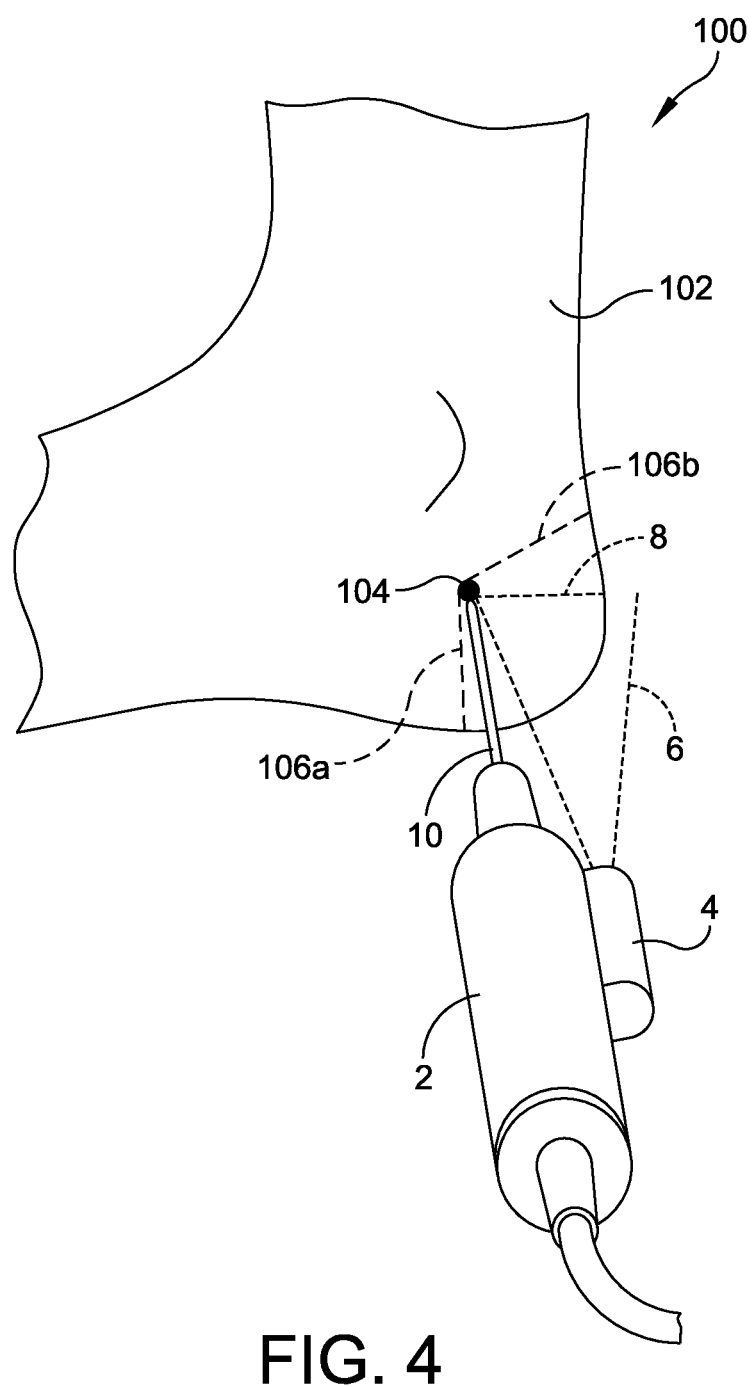
FIG. 4 illustrates the surgical instrument of FIG. 3 in a second position with respect to the target site of FIG. 1, in accordance with some embodiments.

FIG. 4 illustrates the surgical instrument 2 positioned at a second position with respect to the target site 100 such that the emitted marker 8 does not correspond to either guide marker 106a, 106b formed on the surface 112 of the target site 100. The misalignment between the emitted marker 8 and the guide markers 106a, 106b indicates to a surgeon and/or robotic surgery system that the cutting instrument 10 of the surgical instrument 2 is not positioned correctly to perform a desired surgical operation. A surgeon and/or robotic surgery system can adjust the surgical instrument to align the emitted marker 8 with at least one of the guide markers 106a, 106b prior to performing an additional surgical operations. For example, a surgeon and/or robotic surgery system may rotate and pivot the surgical instrument 2 to align the emitted marker 8 with the second guide marker 106b in order to form a second desired cut in a bone.

Figure 5:
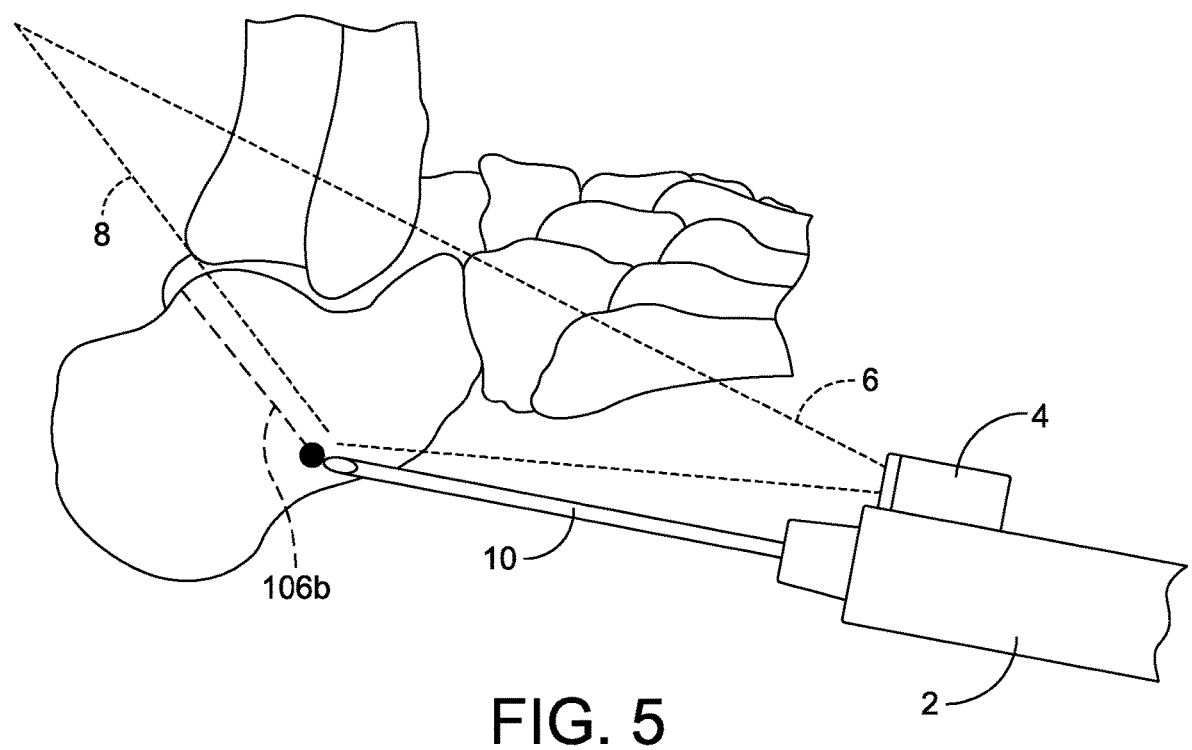
FIG. 5 illustrates an internal view of the target site of FIG. 1 and the surgical instrument of FIG. 3, in accordance with some embodiments.

FIG. 5 illustrates an internal view of the target site 100 and the surgical instrument 2, in accordance with some embodiments. As illustrated in FIG. 5, the position of the emitted marker 8 on the surface 112 of the surgical site 100 may not directly correspond to the position of a guide marker 106c projected onto an internal anatomical structure, such as a calcaneus 110, based on the viewing angle. For example, in the illustrated embodiment, the emitted marker 8 aligns with the guide marker 106c when viewed from an angle corresponding to a longitudinal axis of the surgical instrument 2. Pivoting movement of the surgical instrument 2 causes an opposite pivoting movement of the cutting instrument 10 which will result in a bone cut formed along the line denoted by guide marker 106c.

Figure 6:
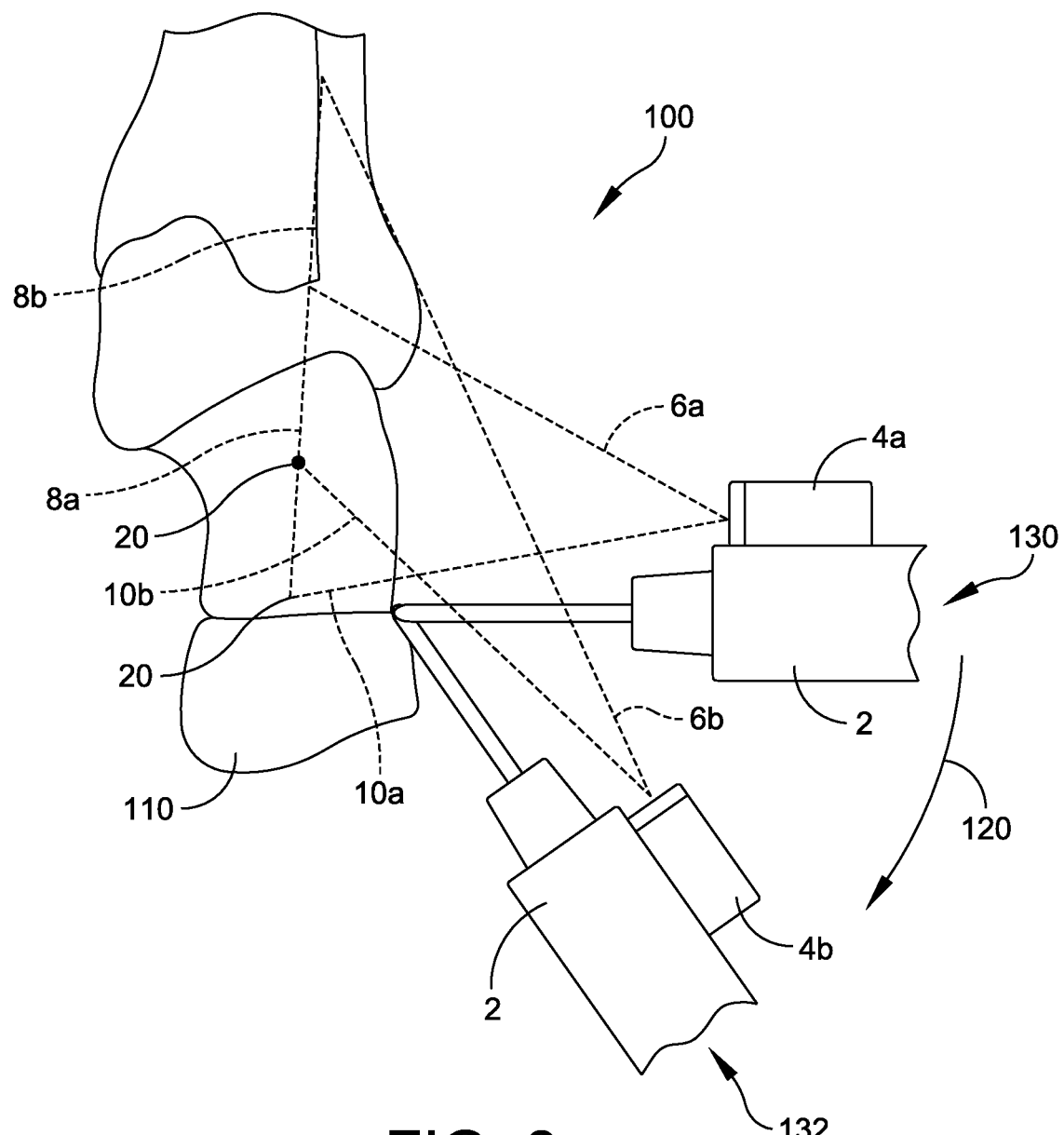
FIG. 6 illustrates a surgical instrument including a laser guide transitioning from a first position to a second position, in accordance with some embodiments.

FIG. 6 illustrates a surgical instrument 2 including a laser guide 4 transitioning from a first position to a second position, in accordance with some embodiments. As illustrated in FIG. 6, the surgical instrument 2 may begin in a first position 130 corresponding to an insertion position of the surgical instrument 2. A laser guide 4 coupled to the surgical instrument 2 is configured to project an emitted guide 8a at a first location on the target site 100. The bottom corned 20 of the emitted guide 8a corresponds to a location of the tip of the cutting instrument 10 and a first edge 22 of the emitted guide 8a corresponds to a predetermined optimal travel path of the cutting instrument 10 to form a first cut in the calcaneus 110. As discussed above, in some embodiments, the surface of the target site 100 includes one or more guide markers 106a, 106b corresponding to cuts or other surgical procedures to be performed.

A surgeon or robotic surgical system pivots the surgical instrument 2 to transition from the first position 130 to a second position 132. Movement of the surgical instrument 2 to the second position 132 relocates the emitted guide 8b to a second location on the target site 100. The bottom corner 20 of the emitted guide 8b continues to denote the position of the tip of the cutting instrument 10. The first edge 22 of the emitted guide 8b illustrates a potential additional movement path for continued pivoting of the surgical instrument 2. The surgeon and/or robotic surgical system may pivot the surgical instrument 2 from the initial, first position 130 until one or more portions of the emitted guide 8b, such as the bottom corner 20, correspond to a predetermined location on the target site 100, such as, for example, a terminal end of a guide marker 106a-106c formed on the surface 112 of a target site 100, indicating that the cutting instrument 10 has reached the predetermined, second location 132. The surgical instrument 2 and/or the laser guide 4 may be repositioned and/or reoriented to relocate the emitted guide 8b to a new location corresponding to one or more additional cuts (or other surgical procedures) to be performed.

Figure 7:
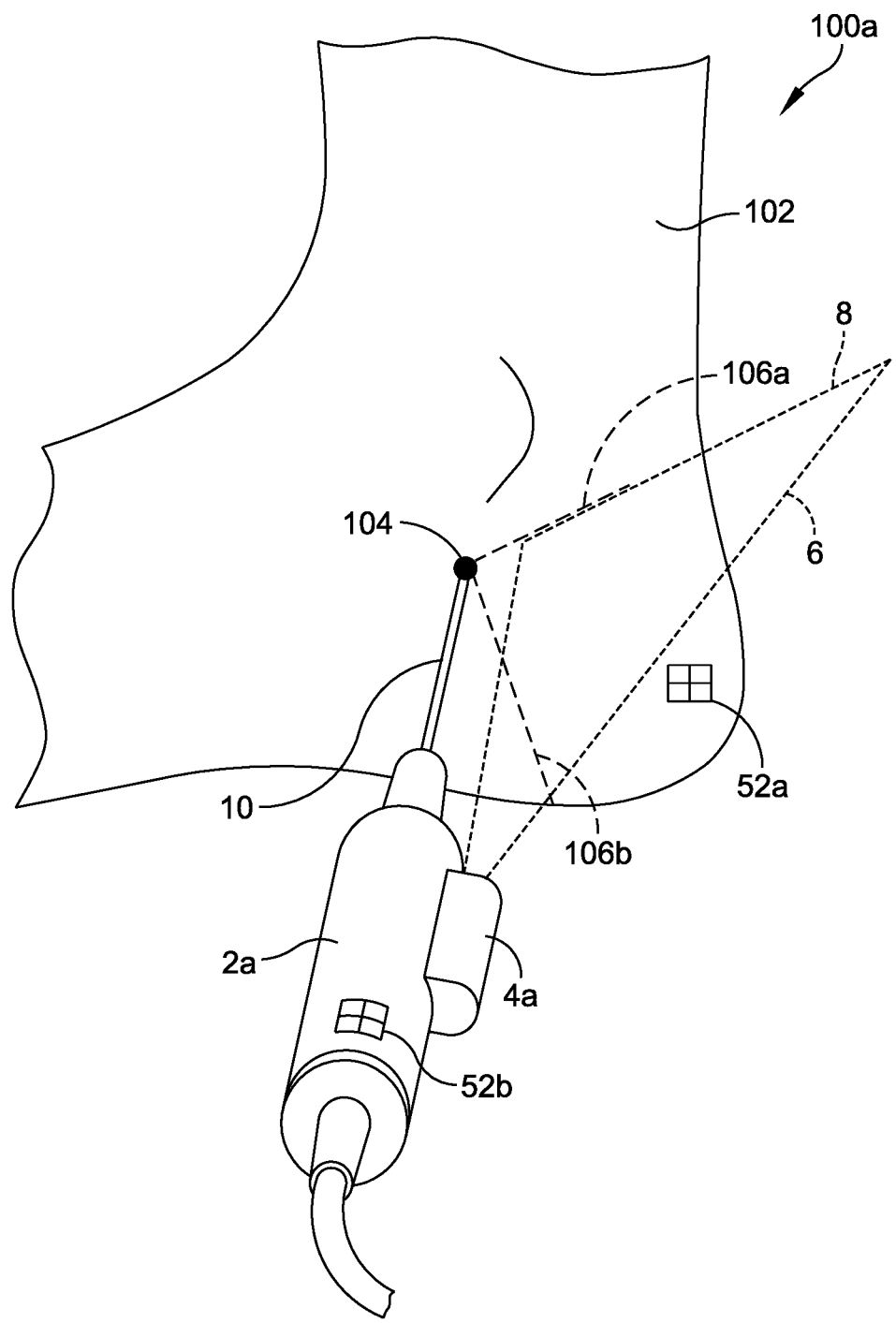
FIG. 7 illustrates a surgical system including a surgical instrument having a laser guide coupled thereto and an position sensor, in accordance with some embodiments.

FIG. 7 illustrates a surgical system 50 including a surgical instrument 2a having a laser guide 4a coupled thereto and at least one position sensor 52a, 52b, in accordance with some embodiments. The surgical instrument 2a is similar to the surgical instrument 2 discussed above and similar description is not repeated herein. Further, the laser guide 4a is similar to the laser guide 4 discussed above and similar description is not repeated herein. The surgical system 50 includes one or more position sensors 52a, 52b. Each of the position sensors 52a, 52b is configured to be coupled to one or more locations at a target site 100a, such as, for example, a surgical instrument 2a, a predetermined position on a surface 112a of the target site 100a, and/or any other suitable location.

The position sensors 52a, 52b may be configured to provide input to one or more control and/or monitoring systems (not shown). For example, in some embodiments, a first position sensor 52a is coupled to a surgical instrument 2a. The first position sensor 52a is configured to provide one or more signals indicative of movement of the surgical instrument 2a. The one or more signals correspond to movement of the surgical instrument 2a in one or more directions and/or planes. For example, in some embodiments, the first position sensor 52a is configured to monitor movement of a surgical instrument 2a in a first plane corresponding to internal pivoting of a cutting instrument 10 coupled to the surgical instrument 2a. The position sensor 52a may be configured to monitor any movement of the surgical instrument 2a in up to six degrees of movement.

As another example, in some embodiments, a second position sensor 52b is coupled to the surface 112 of the target site 100. The second position sensor 52b is configured to provide one or more signals indicative of movement of the target site 100 and/or one or more anatomical structures at the target site 100. For example, in the illustrates embodiment, the second position sensor 52b is configured to generate one or more signals indicative of movement of a foot, although it will be appreciated that the second position sensor 52b may be configured to provide more specific signals, e.g., movement of a calcaneus, and/or more general signals, e.g., movement of a leg. The second position sensor 52b may be configured to monitor any movement of the target site 100 in up to six degrees of movement.

In some embodiments, one or more position sensors 52a, 52b are configured to provide input signals to a monitoring system (not shown). For example, a surgical instrument 2a and/or target site 100 may be positioned at an initial position. Movement of the surgical instrument 2a and/or the target site 100 may be monitored by one or more position sensors 52a, 52b to determine a path of movement of the surgical instrument 2a (such as of a cutting instrument 10) and/or of the target site 100. In some embodiments, the monitoring system is configured to compare movement of the surgical instrument 2a and/or the target site 100 against one or more predetermined movement patterns such as no movement, a line, an area, etc. In some embodiments, the monitoring system is configured to provide a visual, aural, and/or otherwise perceptible indication when the surgical instrument 2a and/or any portion of the surgical instrument 2a (e.g., a cutting instrument 10) deviates from a predetermined movement path or pattern.

In some embodiments, one or more positions sensors 52a, 52b are configured to provide input signals to a robotic surgical control system (not shown). For example, a surgical instrument 2a and/or a target site 100 may be positioned at an initial position with respect to a robotic surgical system. The surgical instrument 2a may be manipulated by the robotic surgical system to perform one or more surgical procedures. The movement of the surgical instrument 2a is detected by the one or more position sensors 52a, 52b and provided to the robotic surgical control system as an input (e.g., feedback) to provide precise control of the surgical instrument 2a. In some embodiments, the robotic surgical system is configured to move of the surgical instrument 2a in one or more predetermined movement patterns such as a line, an area, etc. based on feedback received from one or more position sensors 52a, 52b.

In some embodiments, the one or more position sensors 52a, 52b may be used in conjunction with the laser guide 4a to monitor, guide, and/or confirm movement of a surgical instrument 2a. For example, in some embodiments, a laser guide 4a is configured to generate an emitted marker 8 corresponding to at least one guide marker 106a formed on a surface 112 of a target site 100. The emitted marker 8 may be used to position the surgical instrument 2a at an initial, or starting, position. After positioning the surgical instrument 2a, the emitted marker 8 and one or more signals generated by one or more position sensors 52a, 52b may be configured to provide monitoring and control of internal movement of a surgical instrument 2a, such as movement of a cutting instrument 10. The emitted marker 8 and/or the position sensors 52a, 52b may be configured to generate feedback for a surgeon, robotic-assisted surgical system, and/or robotic surgical system to provide predetermined movement of the surgical instrument 2a to perform one or more surgical operations at the target site 100.

In some embodiments, a first position sensor 52a and at least a second position sensor 52b are configured to monitor relative movement a surgical instrument 2a and a target site 100a during a surgical operation. For example, in some embodiments, the surgical instrument 2a or the target site 100 (e.g., one or more anatomical structures at the target site 100) may be moved during a surgical procedure. The position sensors 52a, 52b may be configured to monitor relative movement to determine if the combined movement of the surgical instrument 2a and the target site 100a correspond to a predetermined movement pattern. In some embodiments, if the combined movement is outside of a predetermined movement pattern, feedback may be generated as discussed above.

The position sensors 52a, 52b may include any suitable position sensors. For example, in various embodiments, the position sensors 52a, 52b may include one or more of an accelerometer, gyroscope, eddy-current sensor, hall effect sensor, inductive sensor, capacitive sensor, piezo-electric sensor, proximity sensor, ultrasonic sensor, and/or any other suitable sensor. In various embodiments, each position sensor 52a, 52b may be replaced by two or more separate position sensors configured to monitor one or more degrees of movement of a surgical instrument 2a, target site 100, and/or other associated structure.

Although the subject matter has been described in terms of exemplary embodiments, it is not limited thereto. Rather, the appended claims should be construed broadly, to include other variants and embodiments, which may be made by those skilled in the art.

What is claimed is:

1. A surgical instrument, comprising:
   a handle having a central axis and at least one handle position sensor configured to detect movement of the handle in at least one degree of freedom;
   a working element extending from the handle substantially along the central axis, the working element configured to be positioned internal of a target site while the handle is external to the target site;
   at least one patient position sensor configured to be coupled to the target site, wherein the patient position sensor is configured to provide one or more signals indicative of movement of the target site in at least one degree of freedom relative to the handle; and
   a laser guide configured to generate at least one emitted marker, wherein the at least one emitted marker corresponds to movement of the working element internal of the target site.

2. The surgical instrument of claim 1, wherein the at least one emitted marker comprises a line denoting a travel path of the working element internal of the target site.

3. The surgical instrument of claim 1, wherein the at least one emitted marker comprises an area defining a resection area.

4. The surgical instrument of claim 1, wherein the at least one emitted marker comprises a linear projection.

5. The surgical instrument of claim 1, wherein the working element comprises a cutting instrument.

6. The surgical instrument of claim 1, wherein the laser guide is configured to maintain a fixed position of the at least one emitted marker in response to movement of the handle.

7. The surgical instrument of claim 1, wherein the laser guide is configured to move the at least one emitted marker opposite of a direction of movement of the handle.

8. The surgical instrument of claim 1, wherein the at least one handle position sensor is in signal communication with a monitoring system configured to monitor movement of the working element with respect to a predetermined movement path.

9. The surgical instrument of claim 1, wherein the handle is configured to be coupled to a robotic surgery system, and wherein the at least one handle position sensor is in signal communication with the robotic surgery system.

10. A system, comprising:
    a surgical instrument, comprising:
    a handle having a central axis;
    a working element extending from the handle substantially along the central axis, the working element configured to be positioned internal of a target site while the handle is external to the target site; and
    a laser guide configured to generate at least one emitted marker, wherein the at least one emitted marker corresponds to movement of the working element internal of the target site; and
    a first position sensor configured to be coupled to a target site, wherein the first position sensor is configured to provide one or more signals indicative of movement of the target site in at least one degree of freedom relative to the surgical instrument.

11. The system of claim 10, comprising a second position sensor coupled to the surgical instrument, wherein the second position sensor is configured to provide one or more signals indicative of movement of the surgical instrument in at least one degree of freedom.

12. The system of claim 11, wherein the second position sensor is in signal communication with a monitoring system configured to monitor movement of the working element with respect to a predetermined movement path.

13. The system of claim 10, wherein the laser guide is configured to maintain a fixed position of the at least one emitted marker in response to movement of the handle.

14. The system of claim 10, wherein the laser guide is configured to move the at least one emitted marker opposite of a direction of movement of the handle.

15. The system of claim 10, wherein the handle is configured to be coupled to a robotic surgery system, and wherein the first position sensor is in signal communication with the robotic surgery system.

* * * * *